United States Patent
Bowe et al.

[11] Patent Number: 6,146,381
[45] Date of Patent: Nov. 14, 2000

[54] CATHETER HAVING DISTAL REGION FOR DEFLECTING AXIAL FORCES

[75] Inventors: Wade A. Bowe, Temecula; Robert C. Hayzelden, Canyon Lake; John A. Simpson, Carlsbad, all of Calif.

[73] Assignee: Cardiac Pacemakers, Inc., St. Paul, Minn.

[21] Appl. No.: 09/073,395

[22] Filed: May 5, 1998

[51] Int. Cl.⁷ .......................... A61B 18/18; A61M 25/00
[52] U.S. Cl. .......................... 606/41; 607/122; 600/374; 600/585; 604/528; 604/530
[58] Field of Search .................... 607/119, 122; 600/372, 373, 374, 585; 604/264, 523, 525, 528, 530; 606/41

[56] References Cited

U.S. PATENT DOCUMENTS

| | | | |
|---|---|---|---|
| 4,498,482 | 2/1985 | Williams | 607/122 |
| 4,917,102 | 4/1990 | Miller et al. | 128/772 |
| 4,960,134 | 10/1990 | Webster, Jr. | 128/786 |
| 5,171,232 | 12/1992 | Castillo et al. | 604/280 |
| 5,383,923 | 1/1995 | Webster, Jr. | 607/125 |
| 5,476,495 | 12/1995 | Kordis et al. | 607/122 |
| 5,487,385 | 1/1996 | Avitall | 128/642 |
| 5,487,757 | 1/1996 | Truckai et al. | 607/122 |
| 5,489,270 | 2/1996 | van Erp | 604/95 |
| 5,522,875 | 6/1996 | Gates et al. | 607/127 |
| 5,531,685 | 7/1996 | Hemmer et al. | 604/95 |
| 5,549,581 | 8/1996 | Lurie et al. | 604/282 |
| 5,582,609 | 12/1996 | Swanson et al. | 606/39 |
| 5,617,854 | 4/1997 | Munsif | 128/642 |
| 5,626,136 | 5/1997 | Webster, Jr. | 128/642 |
| 5,637,090 | 6/1997 | McGee et al. | 604/95 |
| 5,680,860 | 10/1997 | Imran | 606/41 |
| 5,715,817 | 2/1998 | Stevens-Wright et al. | 128/642 |
| 5,807,324 | 9/1998 | Griffin, III | 604/95 |
| 5,823,955 | 10/1998 | Kuck et al. | 600/374 |
| 5,860,920 | 1/1999 | McGee et al. | 600/374 |
| 5,876,385 | 3/1999 | Ikari et al. | 604/523 |
| 5,882,346 | 3/1999 | Pomeranz et al. | 607/122 |

FOREIGN PATENT DOCUMENTS

| | | |
|---|---|---|
| 0790066A2 | 2/1992 | European Pat. Off. . |
| 0745406A2 | 12/1996 | European Pat. Off. ....... A61M 25/00 |
| 0778043A1 | 12/1996 | European Pat. Off. . |
| WO94/21168 | 9/1994 | WIPO . |
| WO926836 | 7/1997 | WIPO . |

*Primary Examiner*—Linda C. M. Dvorak
*Assistant Examiner*—David M. Ruddy
*Attorney, Agent, or Firm*—Fulwider Patton Lee & Utecht, LLP

[57] ABSTRACT

A catheter having a preformed distal shape for positioning a plurality of electrodes at a selected biological site includes a sheath having a preformed bend in the distal end region to distribute axial forces applied, in the distal direction, to the distal end region over a surface area of the distal end region proximal the distal tip. Also included in the catheter sheath is a stylet formed of a material capable of retaining a shape with the distal end of the stylet shaped in the preformed bend. Preferably, the preformed bend is approximately 45 degrees. Axial forces applied to the catheter are deflected to cause bowing of the catheter so that a larger surface area of the catheter contacts the tissue, rather than the smaller surface area of the distal tip. In other aspects, the portion of the sheath coincident with the preformed bend has a lower durometer, the stylet is more flexible by having a reduced diameter and the electrodes are located proximal to the preformed bend.

23 Claims, 6 Drawing Sheets

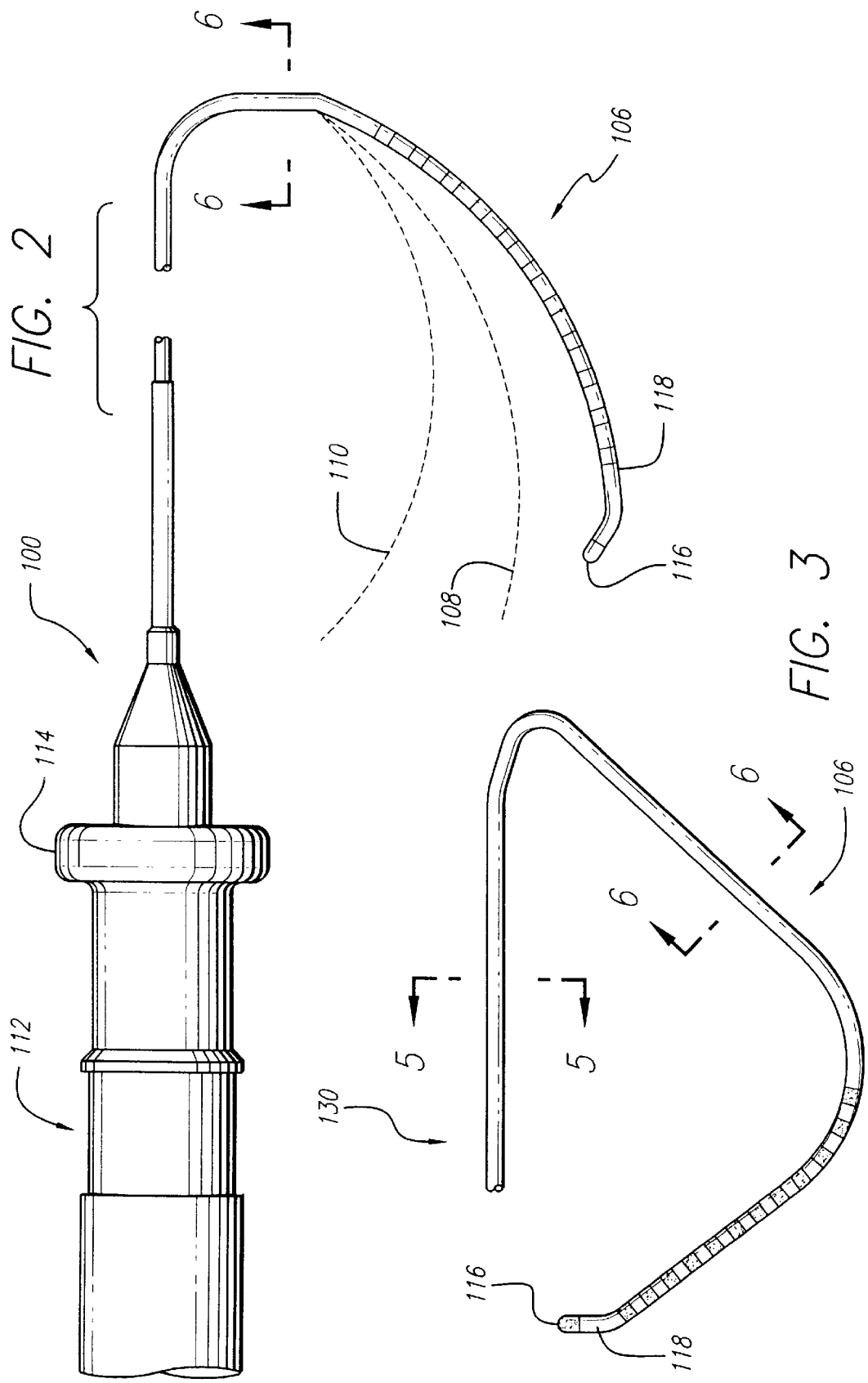

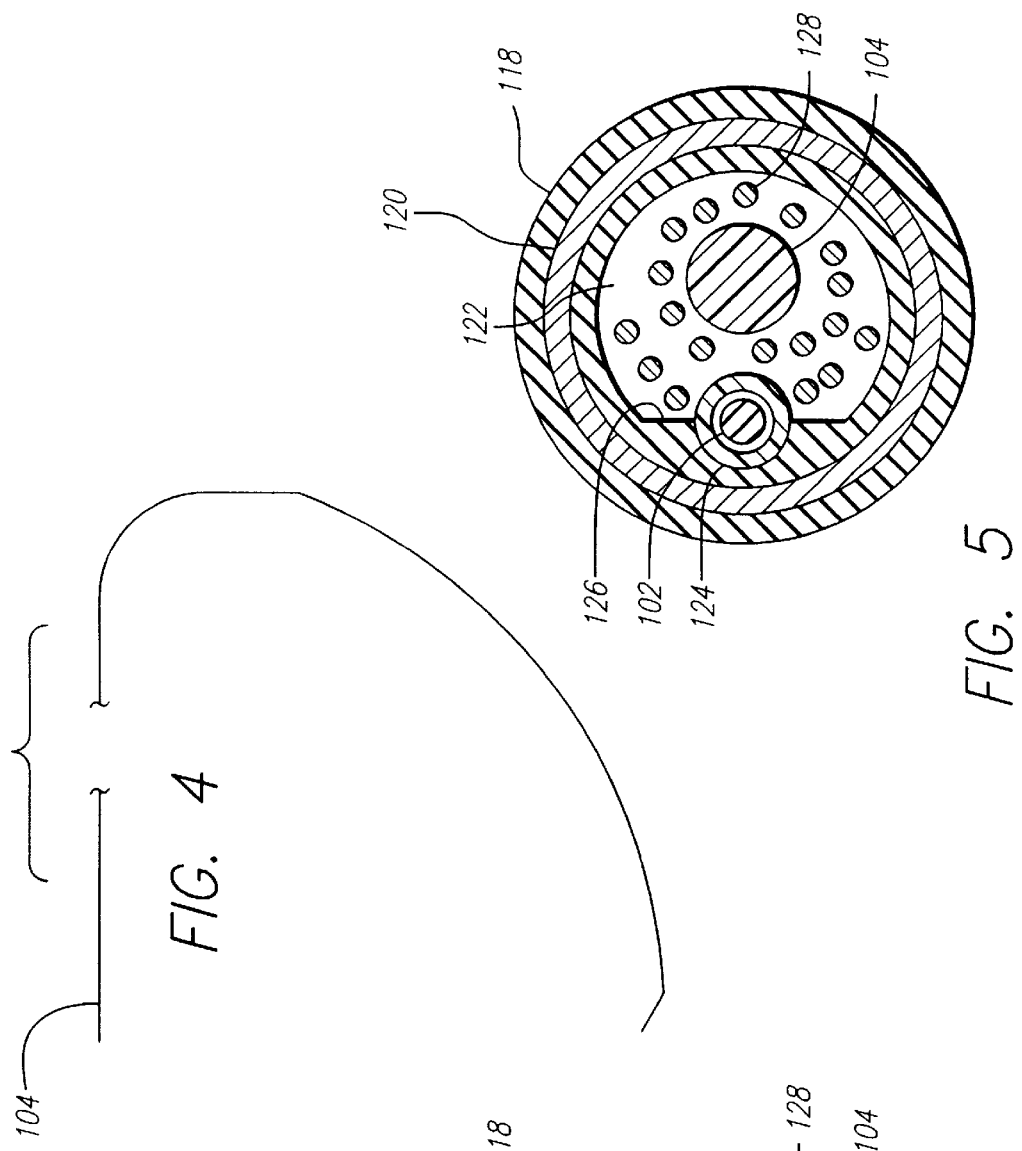
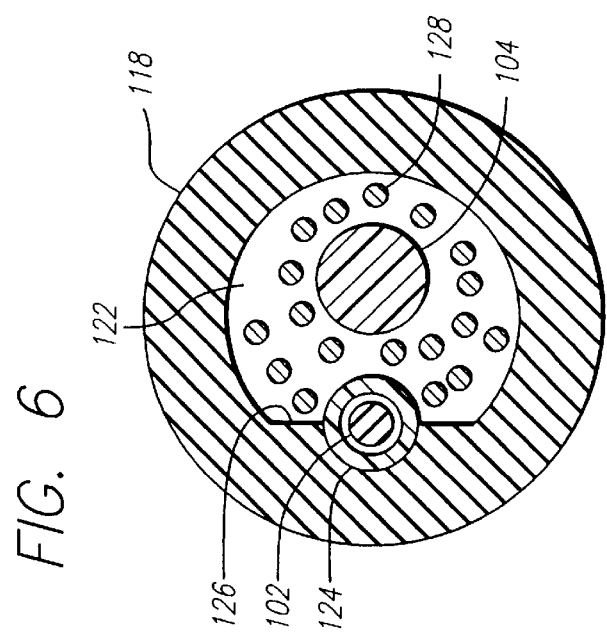

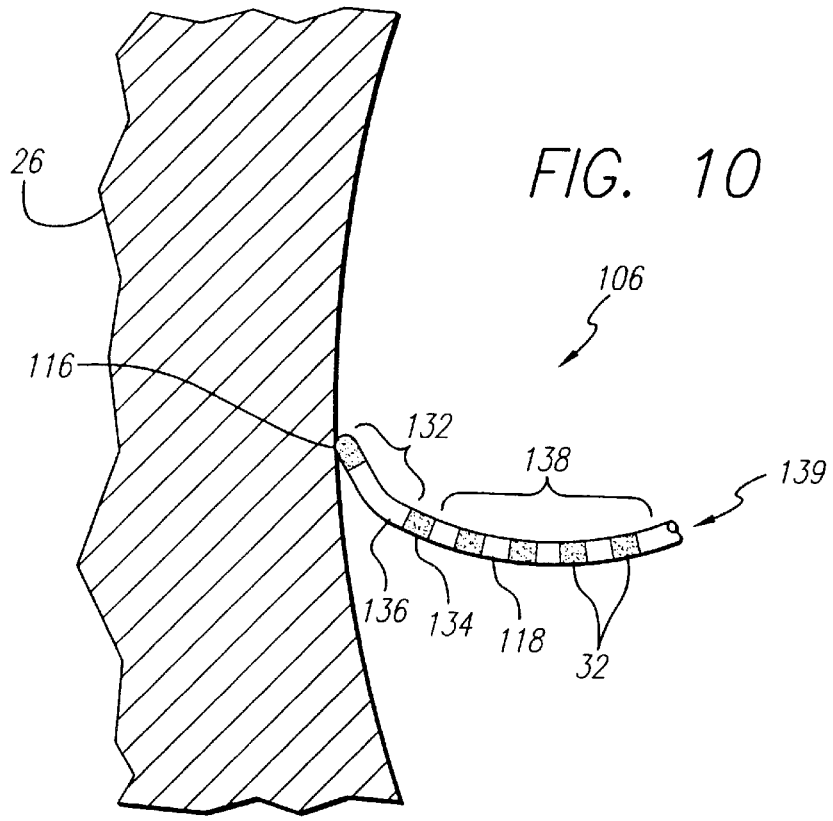
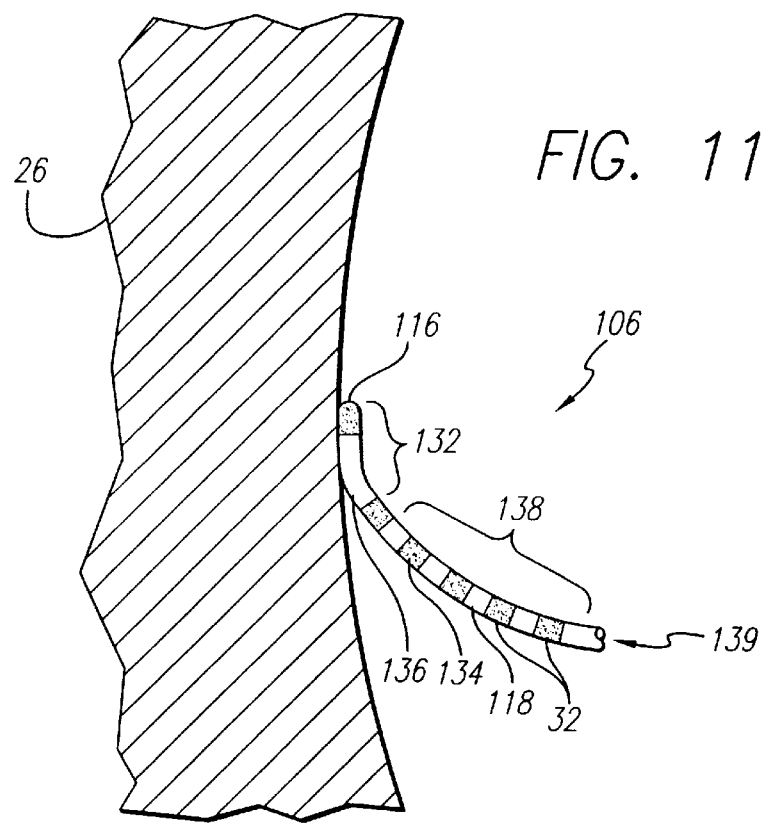

CATHETER HAVING DISTAL REGION FOR DEFLECTING AXIAL FORCES

BACKGROUND OF THE INVENTION

The invention relates generally to an electrophysiological ("EP") apparatus for providing energy to biological tissue, and more particularly, to a catheter having a distal end region constructed for distributing axial forces applied to the catheter, in the distal direction, over an increased surface area relative to the surface area of the distal tip of the catheter.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

A basic configuration of an ablation catheter for applying RF energy includes a distal tip which is fitted with an electrode device. The electrode device is the source of an electrical signal that causes heating of the contacting and neighboring tissue. In the unipolar method, the electrode device may include a single electrode used for emitting RF energy. This single electrode acts as one electrical pole. The other electrical pole is formed by the backplate in contact with a patient's external body part. A RF source is applied to the electrode. The RF source is typically in the 500 kHz region and produces a sinusoidal voltage. When this is delivered between the distal tip of a standard electrode catheter and a backplate, it produces a localized RF heating effect and produces a well defined, deep acute lesion slightly larger than the tip electrode.

In other techniques, used in the treatment of atrial fibrillation, a plurality of spaced apart electrodes are located at the distal end of the catheter. RF energy is applied by the electrodes to the heart tissue to produce a long lesion. In an attempt to ensure intimate contact between the electrode and the target tissue the distal end of the catheter may have a preformed shape complementary or almost complementary to the expected heart tissue shape. To maintain such a shape a preformed stylet may be placed within the catheter. Typically the stylet is formed of a relatively large diameter wire having sufficient strength so that when the catheter is placed in the targeted anatomical location the catheter adequately resists unwanted distortion. The large diameter stylet also gives the catheter sufficient rigidity so that it can be satisfactorily manipulated by pushing, torquing etc. in order to improve electrode contact as needed. However, this increased rigidity may permit the application of higher axial forces to the tissue by the distal tip of the catheter. If the distal tip were in end-on contact with the heart tissue, axial forces applied to the proximal end of the catheter external to the patient may be transferred to the heart tissue by the more rigid catheter shaft through the end-on contact. Should an end-on contact of the distal tip to heart tissue occur while at the same time significant axial force is applied, heart tissue may be adversely affected. Thus, it is desirable to limit the amount of axial force that can be applied to heart tissue by the catheter in an end-on mode.

Hence, those skilled in the art have recognized a need for a catheter having a distal end region with sufficient rigidity such that the distal end region may be introduced into a biological cavity and intimate contact maintained between the electrodes of the distal end region and the tissue while at the same time having a structure such that excessive axial forces applied to the catheter, in the distal direction, are distributed over a surface area of the distal end region proximal the distal tip and are prevented from concentrating at the distal tip of the catheter. The invention fulfills these needs and others.

SUMMARY OF THE INVENTION

Briefly, and in general terms, the invention is directed to an apparatus for applying energy to biological tissue. The apparatus has a preformed shape with increased rigidity but also a form that prevents axial forces from concentrating at the distal tip of the catheter and instead distributes the forces along the distal end region thereby reducing adverse effects to the tissue by allowing the distal shape to deflect and conform to the tissue geometry.

In a first aspect, the invention is a catheter having a sheath with a distal end region and a distal tip at the distal extremity of the distal end region, for use with biological tissue. The catheter comprises a working region located in the distal end region and proximal the distal tip, the working region has an energy transfer device for transferring energy between the biological tissue and the catheter. Also included are means for distributing axial forces applied to the distal end region in the distal direction over a surface area of the distal end region proximal the distal tip.

In a detailed aspect the surface area over which the axial forces are distributed is larger than the surface area of the distal tip. In another detailed aspect, the means for deflecting comprises a preformed bend located between the distal tip and the working region. In further aspects, the means for deflecting further comprises the sheath having a lower durometer at the location of the preformed bend and further comprises an area of the sheath having reduced wall thickness at the location of the preformed bend. Further, the sheath has increased flexibility at the preformed bend.

In more detailed aspects, the distal tip comprises a tip component having a proximal end and the preformed bend is located approximately 1 cm proximal the proximal end of the tip component. The preformed bend is approximately forty-five degrees in one aspect and is within the range of ten to eighty degrees in another aspect.

In yet more detailed aspects, a stylet is housed within the sheath, the stylet having a preformed shape comprising a first bend and a second bend with the first bend being equal to the preformed bend. The stylet is mounted within the sheath such that the first bend is coincident with the preformed bend of the sheath. The stylet is formed and mounted in the sheath such that the sheath takes the form of the stylet. In a further aspect, the stylet is formed with greater flexibility at the first bend. In yet a further aspect, a tendon is housed within the sheath and attached at the distal end of the catheter, wherein axial movement of the tendon results in deflection of the distal end region of the catheter. The tendon is mounted in the sheath such that so that pulling the tendon in the proximal direction decreases the radius of curvature of the distal end region and movement of the tendon in the distal direction increases the radius of curvature of the distal end region. In a more detailed aspect, the stylet and tendon are attached to the tip component.

In another aspect, the working region of the catheter includes a plurality of spaced-apart electrodes wherein a first electrode is spaced from the distal tip a distance greater than the distance between the preformed bend and the distal tip. The electrodes are spaced apart from each other by approximately 4 mm and the first electrode is spaced approximately 1.5 cm from the distal tip.

In a second aspect, the invention is a catheter having a sheath with a distal end region and a distal tip at the distal extremity of the distal end region, for use with biological tissue. The catheter comprises a working region located on the distal end region and proximal the distal tip, the working region has an energy transfer device for transferring energy between the biological tissue and the catheter. Also included is a preformed bend located between the distal tip and the working region, the preformed bend has an angle selected so that a portion of the distal end region is deflected when the distal end region of the sheath contacts the biological tissue and an axial force, that reaches a predetermined threshold, is applied to the distal end region in the distal direction.

In a third aspect, the invention is a catheter for use in ablating tissue in the heart of a patient, the catheter has a sheath with a distal end region which has a preformed distal shape, and a distal tip at the distal extremity of the distal end region. The catheter comprises a plurality of electrodes mounted to the sheath in a working region within the distal end region, a stylet housed within the sheath, the stylet formed of a material that retains the preformed distal shape, and a tendon housed within the sheath and attached to the distal end of the sheath and positioned for axial displacement. Also included is a preformed bend in the catheter sheath located between the distal tip and the first electrode of the working region. The preformed bend has an angle selected so that a portion of the catheter sheath located proximal the distal tip is deflected when the distal end region of the sheath contacts the heart tissue and an axial force, that reaches a predetermined threshold, is applied to the catheter sheath in the distal direction.

These and other aspects and advantages of the invention will become apparent from the following detailed description and the accompanying drawings, which illustrate by way of example the features of the invention.

BRIEF DESCRIPTION OF THE DRAWINGS

FIG. 2 is a diagram of a catheter system including a handle, steering member, and a catheter having a preformed distal end region with a first shape;

FIG. 3 is an alternate preformed distal end region of FIG. 2 having a second shape;

FIG. 4 is a preformed stylet for shaping the distal end region of the catheter of FIG. 2;

FIG. 5 is a sectional view of the proximal region of the catheter of FIG. 3 taken along the line 5—5 depicting the catheter sheath with braid, stylet, steering tendon and leads;

FIG. 6 is a sectional view of the distal end region of the catheter of FIGS. 2 and 3 taken along the line 6—6 depicting the catheter sheath, stylet, steering tendon and leads;

FIG. 10 is a representation of the distal end region of the catheter of FIG. 3 with the distal tip contacting the tissue; and FIG. 11 is a representation of the distal end region of the catheter of FIG. 3 showing the effect that the preformed bend has upon the catheter when axial forces exceeding a predetermined threshold are applied to the catheter.

DETAILED DESCRIPTION OF PREFERRED EMBODIMENTS

Figure 1:
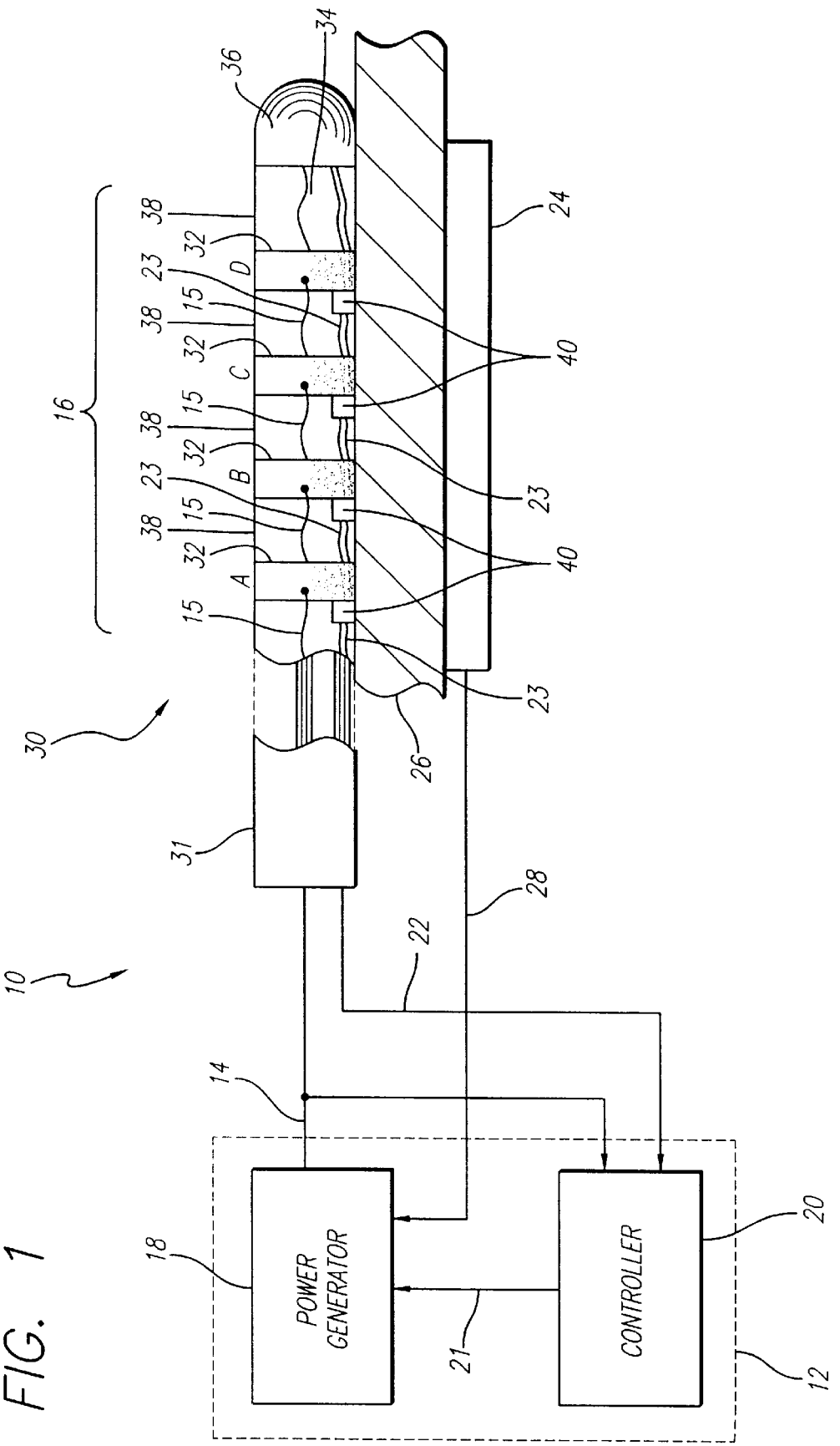
FIG. 1 is a schematic diagram of an ablation apparatus including a power control system, electrode device and backplate.

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive 14 to an electrode device 16. The power control system 12 comprises a power generator 18 that may have any number of output channels through which it provides the power 14. The operation of the power generator 18 is controlled by a controller 20 which outputs control signals 21 to the power generator 18. The controller 20 monitors the power 14 provided by the power generator 18. In addition, the controller 20 also receives temperature signals 22 from the electrode device 16. Based on the power 14 and temperature signals 22 the controller 20 adjusts the operation of the power generator 18. A backplate 24 is located proximal to the biological site 26 opposite the site from the electrode device 16, and is connected by a backplate wire 28 to the power generator 18. The backplate 24 is set at the reference level to the power provided to the electrodes, as discussed in detail below.

In a manual arrangement, the temperature sensed and/or the determined impedance may be displayed to an operator. The operator in response may then manually control the duty cycle or other power parameters such as by rotating a knob mounted on a front panel of an instrument. In the case of a multiple channel instrument and catheter, as discussed below, multiple knobs may be provided in this manual arrangement for control over each channel.

The electrode device 16, i. e. energy transfer device, is typically part of a steerable EP catheter 30 capable of being percutaneously introduced into a biological site 26, e. g., the atrium or ventricle of the heart. The electrode device 16 is shown in schematic form with the components drawn to more clearly illustrate the relationship between the components and the relationship between the components and the power control system 12. In this embodiment, the catheter 30 comprises a distal segment 34 and a handle 31 located outside the patient. A preferred embodiment of the electrode device 16 includes twelve band electrodes 32 arranged in a substantially linear array along the distal segment 34 of the catheter 30. The electrode device 16 may include a tip electrode 36. (For clarity of illustration, only four band electrodes 32 are shown in the figures although as stated, a preferred embodiment may include many more.) The band electrodes 32 are arranged so that there is space 38 between adjacent electrodes. In one configuration of the electrode device 16, the width of the band electrodes 32 is 3 mm and the space 38 between the electrodes is 4 mm. The total length of the electrode device 16, as such, is approximately 8 cm.

The arrangement of the band electrodes 32 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter 30 and also lessens the size of the catheter.

The band electrodes 32 are formed of a material having a significantly higher thermal conductivity than that of the biological tissue 26. Possible materials include silver, copper, gold, chromium, aluminum, molybdenum, tungsten, nickel, platinum, and platinum/10% iridium. Because of the difference in thermal conductivity between the electrodes 32 and the tissue 26, the electrodes 32 cool off more rapidly in the flowing fluids at the biological site. The power supplied to the electrodes 32 may be adjusted during ablation to allow for the cooling of the electrodes while at the same time allowing for the temperature of the tissue to build up so that ablation results. The electrodes 32 are sized so that the surface area available for contact with fluid in the heart, e. g., blood, is sufficient to allow for efficient heat dissipation from the electrodes to the surrounding blood. In a preferred embodiment, the electrodes 32 are 7 French (2.3 mm in diameter) with a length of 3 mm.

The thickness of the band electrodes 32 also affects the ability of the electrode to draw thermal energy away from the tissue it contacts. In the present embodiment, the electrodes 32 are kept substantially thin so that the electrodes effectively draw energy away from the tissue without having to unduly increase the outer diameter of the electrode. In a preferred embodiment of the invention, the thickness of the band electrodes is 0.05 to 0.13 mm (0.002 to 0.005 inches).

Associated with the electrode device 16 are temperature sensors 40 for monitoring the temperature of the electrode device 16 at various points along its length. In one embodiment, each band electrode 32 has a temperature sensor 40 mounted to it. Each temperature sensor 40 provides a temperature signal 22 to the controller 20 which is indicative of the temperature of the respective band electrode 32 at that sensor. In another embodiment of the electrode device 16 a temperature sensor 40 is mounted on every other band electrode 32. Thus for a catheter having twelve electrodes, there are temperature sensors on six electrodes. In yet another embodiment of the electrode device 16 every other electrode has two temperature sensors 40. In FIG. 1, which shows an embodiment having one temperature sensor for each electrode, there is shown a single power lead 15 for each electrode 32 to provide power to each electrode for ablation purposes and two temperature leads 23 for each temperature sensor 40.

In order to ensure a long, continuous lesion the catheter employs a steering tendon and a stylet having a preformed distal shape. As shown in FIG. 2, the catheter 100 includes a distal end region 106 having a preformed distal shape. This distal shape may have any form which generally conforms to the contour of the biological cavity containing the tissue to be ablated. The distal end region 106 of FIG. 2 has been simplified for clarity to depict varying degrees of curvature 108 and 110 obtainable by use of the preformed shape and the steering tendon, as explained below. The distal shape of FIG. 3 is conducive to the treatment of atrial fibrillation in that its shape allows for the distal end region 106 to be easily inserted into the atrium of the heart. The shape, in combination with a steering tendon, also provides a distal end region having a contour which may be adjusted to conform to the contour of the atrium.

The catheter 100 also includes a handle 112 and a steering member 114. A tip component 116 is mounted to a sheath 118 at the very distal tip of the sheath. A shaped-memory wire, i. e., stylet, 104 (FIG. 4) is located in the distal end region 106 and preferably runs the entire length of the sheath 118. The stylet 104 is attached to the tip component 116 at the axis of the tip component, and is anchored to a fixed position within the handle 112. The shaped memory wire 104 is formed of an alloy which exhibits a martensitic phase transformation. Such alloys include those which exhibit non-linear superelasticity (typically Ni-Ti with Ni at 49–51.5% atomic) and those which exhibit linear superelasticity (typically Ni-Ti in near equi-atomic composition which has been cold worked). Preferably, the preformed shaped wire 104 is formed of nitinol wire having a diameter in the range of 0.026 to 0.030 mm and a nitinol composition of 49–51.5% Ni. The shape of the distal end region 106 is created by restraining the nitinol wire in the desired shape and heating the wire to approximately 500° C. for about 10 minutes. The nitinol is then allowed to cool. Upon cooling, the wire 104 retains the preformed distal shape.

Stress may be applied to the wire to change its shape. For example, the wire 104 may be straightened to negotiate an introducer or various blood vessels on its way to the right or left atrium of the heart. Upon removal of the straightening forces, such as when the distal end enters the left atrium of the heart, the stylet accurately resumes its preformed shape causing the distal end of the catheter sheath surrounding it to likewise take the same shape. Because of the superelasticity of the nitinol, once the stress is removed the wire returns to its original shape. This is distinct from other shape-memory materials which are temperature actuated.

Referring now to FIG. 5, the stylet 104 is housed inside a composite sheath 118 constructed of different durometers of Pebax and braided stainless steel ribbon in order to tailor the torsinal and bending stiffness in various locations along the length of the catheter. In the region 130 proximal from the distal end region 106, as shown in FIG. 3 the sheath 118 is formed of high durometer Pebax outer jacket having an outside diameter of 2.39 mm (0.094 inches) (7 French) and an inside diameter of 1.58 mm (0.062 inches). Imbedded within the sheath 118 are two layers of braid, 0.001×0.006 stainless steel ribbon 120. The inner lumen 122 has a hollow PTFE tendon sheath 124 bonded to one side 126. The tendon sheath 124 has an outside diameter of approximately 0.457 mm (0.018 inches). The remaining portion of the tendon sheath 124 is exposed in the inner lumen 122. The steering tendon 102 is housed within the tendon sheath 124 and is formed of a stainless steel wire having a diameter of approximately 0.23 mm (0.009 inches). At its distal end, the steering tendon 102 is attached to the tip component 116 at a point parallel to the axis of the tip component. In the alternative, the steering tendon 102 may be anchored at a point proximal the tip component 116. At its proximal end, the tendon 102 is linked to the steering member 114 (FIG. 2) which translates axially along the length of the handle 112. Also housed within the inner lumen 122 are the leads 128. Eighteen are depicted in FIG. 4, however, more or fewer may be included depending on the number of electrodes 32 and the configuration of the temperature sensors.

In the distal end region 106 (FIGS. 2 and 3), as shown in cross section in FIG. 6, the construction of the sheath 118 is generally the same as that of the proximal region 130 except the outer jacket does not include a stainless steel braid 120. By not including the braid 120, the distal end region 106 is more flexible than the proximal region 130. Accordingly, the distal end region 106 is more easily bent for conformance with the biological site. Housed within the sheath 118 and offset from the axis of the sheath is the steering tendon 102.

Figure 7:
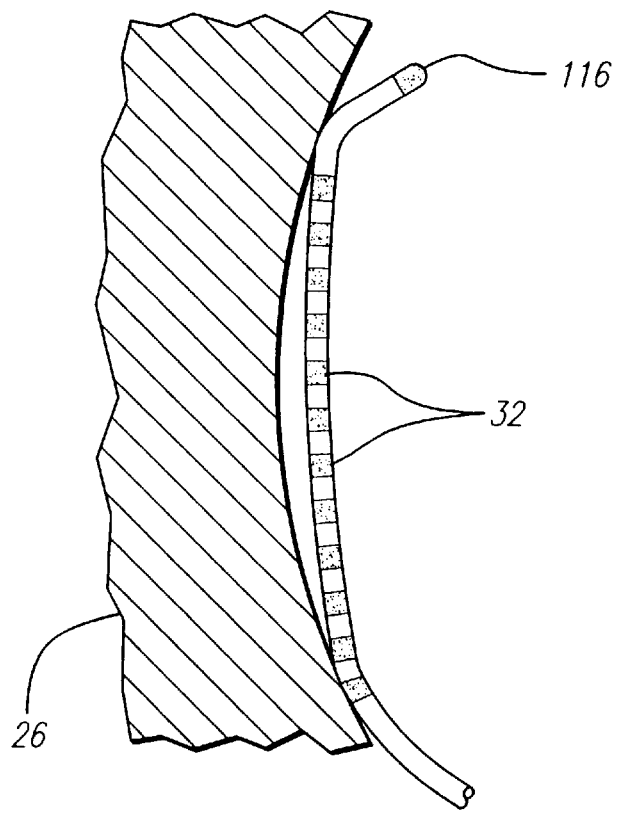
FIG. 7 is a representation of the distal end region of the catheter of FIG. 2 proximal biological tissue with the electrodes not in intimate contact with the tissue.

In operation, the catheter 100 is inserted into the biological cavity containing the tissue to be ablated. In the case of the left atrium where a transseptal approach is used, the catheter may be inserted using an introducer sheath (not shown). The introducer sheath is positioned within the cavity and the catheter 100 is inserted into the introducer sheath. Because of the flexibility of the nitinol stylet 104, the distal end region 106 of the catheter conforms to the shape of the introducer sheath and follows the tortuous path of the introducer sheath. Once the distal end region 106 of the catheter enters the biological cavity the catheter is either extended beyond the distal tip of the introducer sheath or the introducer sheath is retracted. In either case, the distal end region 106 of the catheter is no longer constrained by the introducer sheath and returns to its original preformed distal shape. Once the preformed distal shape is resumed, the distal end region 106 has a shape more closely following that of the heart. However it may not conform to the shape of the biological site 126 as closely as desired. This situation is shown in FIG. 7. Accordingly, some or all of the electrodes 32 may not be in intimate contact with the tissue 26 to be ablated. If the electrodes 32 are not in the desired contact with the tissue 26, the radius of curvature of the distal end region may be adjusted using the steering tendon such that more of the electrodes contact the biological tissue 26. The dashed lines 108 and 110 of FIG. 2 are examples of how the degree of curvature of the distal end region 106 may be adjusted by use of the steering tendon. This adjustment is performed by axially displacing the steering member 114 in the proximal direction. In doing so, the steering tendon 102 attached to the tip component 116 experiences tension and causes the sheath 118 to compress on the side in which the steering tendon is positioned and to stretch on the opposite side. This causes the radius of curvature of the distal end region to decrease as shown in FIG. 2. In addition, to further ensure intimate contact between the electrodes 32 and the tissue 26, the handle 112 may be rotated. Because of the attachment of the sheath 118 to the handle 112 and the construction of the catheter, as previously described in relation to FIGS. 5 and 6, this rotational force at the handle causes the catheter to experience a torquing effect along its length, which may aid in positioning the electrodes against the tissue.

Figure 8:
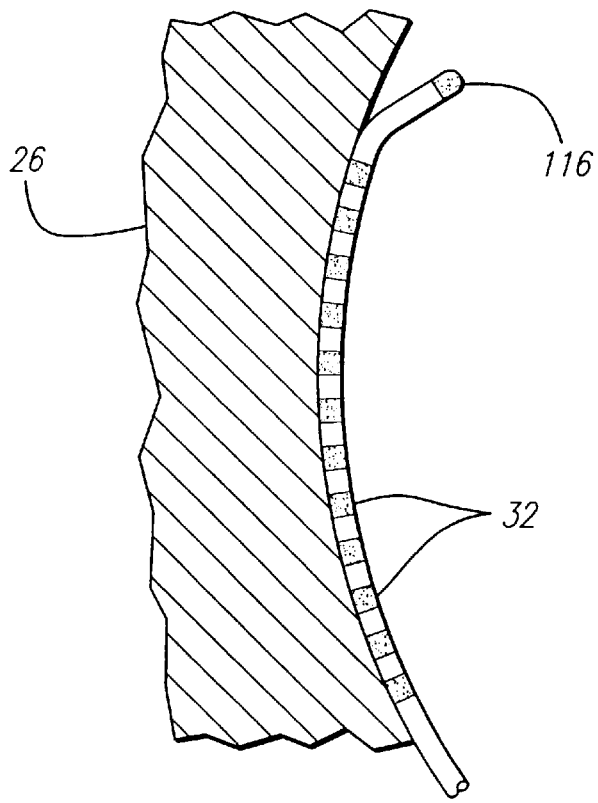
FIG. 8 is a representation of the distal end region of the catheter of FIG. 2 proximal biological tissue with the electrodes in intimate contact with the tissue.

Once the distal end region 106 is properly positioned and the electrodes 32 are in intimate contact with the tissue, as shown in FIG. 8, RF energy is applied to the electrodes to ablate the tissue. After applying energy to a first portion of tissue 26 located within the selected biological cavity, the distal end region 106 of the catheter may be repositioned proximal another region of tissue and the curvature of the distal end region adjusted so that the electrode 32 contact the tissue. Thus, the catheter provides for ready adjustment of the electrode carrying region 106 such that a plurality of electrodes aligned in a substantially linear array may be placed in intimate contact with tissue 26 to be ablated. Because of the length of the linear electrode array, the device shown in the drawings and described above is particularly suited for performing the Maze procedure in a minimally invasive way.

While certain shapes of the distal end of the catheter are shown in FIGS. 2 and 3, other shapes may be used. The invention is not confined to the shapes shown in these figures. Additionally, the steering tendon may be used by the operator to steer or assist in advancing the catheter distal end through the blood vessels of the patient to the desired target tissue.

Figure 9:
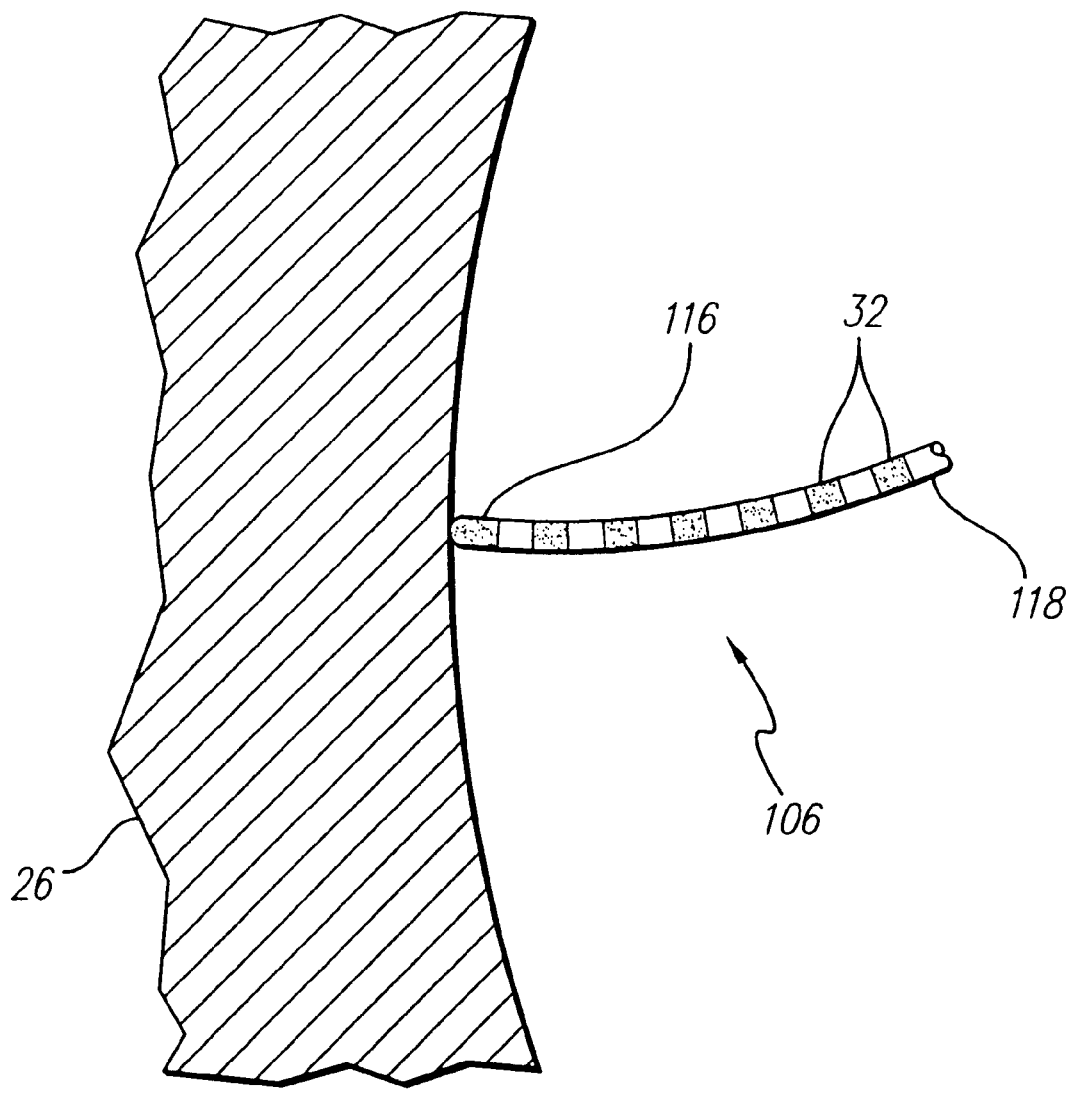
FIG. 9 is a representation of the distal end region of the catheter shown in FIG. 2 with the distal tip in an end-on contact configuration with target tissue.

During operation, the distal tip 116 of the catheter may come into contact with biological tissue 26. Because of the increased rigidity and increased column strength of the catheter 118 caused by the mounting of the stylet 104 within the sheath, the catheter is capable of transmitting much higher axial forces to that tissue 26. Should the catheter sheath 118 be located inside a heart chamber such that an end-on orientation is assumed by the distal tip 116 of the catheter with the heart tissue 26, large axial forces may be applied to that tissue with adverse consequences. Thus, it is desirable to limit the amount of axial force that can be applied to the tissue by the distal tip 116 to a predetermined threshold. A catheter formed as shown in FIG. 2 is capable of being placed in an end-on contact configuration with the target tissue, as shown in FIG. 9, which is generally undesirable. The application of axial force to the catheter shown in FIG. 9 may cause the distal tip 116 of the catheter to apply unacceptably high pressures against the tissue 26.

In accordance with the embodiment shown in FIG. 10, the distal end region 106 of the catheter is constructed such that axial forces are distributed over a larger surface area. The distal end has a preformed bend 136 formed in it. This bend 136 is formed during the formation of the stylet 104 by including a bend in the distal end region of the stylet. The local radius of curvature in the region around the preformed bend 136 is smaller, i. e. a tighter curve, than the working region 138 which carries the electrodes 32. In one embodiment, the preformed bend 136 is 45 degrees in relation to the axis of the most adjacent or first electrode 134. However, depending on the preformed shape of the sheath at the working region and the region proximal to the working region, the angle may range from 10 to 80 degrees. Additionally, in the embodiments shown, the angle is inward. That is, the preformed bend is formed so that the distal tip is directed towards the center of the working region 138 bend. Furthermore, the preformed bend may take any form which effectively reduces the possibility of the distal tip 116 contacting the tissue 26 head on. This form may be an arc instead of an acute angle and may be, for example, a 180 degree arc.

By including the preformed bend 136, the catheter is provided with a point of focus which facilitates the distribution of axial forces applied to the catheter across a larger surface area of the distal end region 106. As shown in FIGS. 10 and 11, the preformed bend 136 causes axial forces 139 applied to the catheter to be redirected into bending the distal end of the catheter rather than concentrating the forces at the distal tip 116 against the tissue. As shown in FIG. 11, the application of axial force 139 causes the distal tip to rotate in relation to the heart tissue 26 with the sheath proximal to the tip bending and moving toward the tissue. If the axial force 139 is continued, the outside side of the sheath 118 eventually makes contact with the tissue and provides a much larger surface area of the catheter to make contact with the tissue and thereby distributes forces across a larger area. As shown in FIG. 11, the working area 138 of the catheter has started to bow outward slightly thus deflecting the axial forces 139.

To enable the easier assembly of the stylet 104 having the preformed bend 136, with the distal tip 116, the preformed bend is located approximately 1 cm from the proximal end of the distal tip electrode 116. This provides enough length of the stylet to attach to the distal tip.

Alternate ways of increasing the flexibility of the distal tip at the preformed bend 136 so that axial forces are deflected include reducing the diameter of the stylet 104 in the bend region 136 and/or reducing the durometer of the outer sheath 118 also in the bend region 136. Another way, as mentioned previously, is to end the braid 120 prior to the preformed bend 136. As discussed in the embodiment above, the catheter sheath 118 in the region of the distal end 106 does not include the stainless steel braid 120. As a result, this region of the catheter is more flexible than the proximal region 130. A further step is to place the electrodes proximal to the preformed bend 136 so that the increased rigidity of the sheath caused by the metallic electrodes 32 is located proximal to the bend 136. In one embodiment, the first electrode 134 is located 1.5 cm from the proximal end of the distal tip electrode.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter for use with biological tissue, said catheter comprising:

a sheath including a distal end region having a distal tip;

a working region located in the distal end region of the sheath and proximal the distal tip, the working region having an energy transfer device for transferring energy between the biological tissue and the catheter;

a stylet housed within the sheath and attached to the distal end region of the sheath, the stylet having a distal end region having a preformed shape comprising a bend, the stylet formed of a shape-retentive and resilient material such that the stylet distal end region changes shape upon the application of force and upon the removal of force, returns to the preformed shape, the stylet disposed in the sheath such that the stylet distal end region is located in the sheath distal end region and causes the sheath distal end region to assume the preformed shape; and a tendon housed within the sheath and attached to the sheath distal end region, wherein movement of the tendon in the proximal direction decreases the radius of curvature of the stylet distal end region and sheath distal end region distal the bend to present a surface area, larger than the surface area of the distal tip, for contact with the tissue.

2. The catheter of claim 1 wherein the sheath has a lower durometer at the location of the bend.

3. The catheter of claim 1 wherein an area of the sheath has reduced wall thickness at the location of the bend.

4. The catheter of claim 1 wherein:

the distal tip comprises a tip component having a proximal end; and the bend is located approximately 1 cm proximal the proximal end of the tip component.

5. The catheter of claim 1 wherein the bend is approximately forty-five degrees.

6. The catheter of claim 1 wherein the bend is within the range of ten to eighty degrees.

7. The catheter of claim 1 wherein for a given movement of the tendon in the proximal direction, the decrease in the radius of curvature of the distal end region distal the bend is greater than the decrease in the radius of curvature of the distal end region proximal the bend.

8. The catheter of claim 1 wherein the stylet is formed with greater flexibility at the bend.

9. The catheter of claim 1 wherein the stylet has a reduced diameter in the region distal the bend.

10. The catheter of claim 1 wherein the distal tip comprises a tip component and the stylet and tendon are attached to the tip component.

11. The catheter of claim 1 wherein the working region includes a plurality of spaced-apart electrodes wherein a first electrode is spaced from the distal tip a distance greater than the distance between the bend and the distal tip.

12. The catheter of claim 11 wherein the electrodes are spaced apart from each other approximately 4 mm.

13. The catheter of claim 12 wherein the first electrode is spaced approximately 1.5 cm from the distal tip.

14. A catheter for use with biological tissue, said catheter comprising:

a sheath with a distal end region and a distal tip at the distal extremity of the distal end region, the distal end region having a deflection region proximal and proximate the distal tip and a working region proximal and proximate the deflection region the working region having an energy transfer device for transferring energy between the biological tissue and the catheter;

a stylet disposed within the sheath, the stylet having a first portion located within the working region, the first portion having a first diameter, the stylet further having a second portion disposed within the deflection region of the sheath and passing therethrough, the diameter of the second portion of the stylet being less than the first diameter, the second portion of the stylet also having a preformed shape comprising a bend, the stylet disposed in the sheath such that the stylet causes the sheath to assume the preformed shape, the stylet formed of a shape-retentive and resilient material such that the first and second portions of the stylet change shape upon the application of force and upon the removal of force, return to their original shapes; and a tendon housed within the sheath and attached to the distal tip of the catheter, wherein movement of the tendon in the proximal direction decreases the radius of curvature of the first and second portions of the stylet.

15. The catheter of claim 14 wherein the sheath in the deflection region has a lower durometer than the sheath in the working region.

16. The catheter of claim 14 wherein the sheath in the deflection region has reduced wall thickness relative to the sheath in the working region.

17. The catheter of claim 14 wherein:

the distal tip comprises a tip component having a proximal end; and the bend is located approximately 1 cm proximal the proximal end of the tip component.

18. The catheter of claim 14 wherein for a given movement of the tendon in the proximal direction, the decrease in the radius of curvature of the second portion of the stylet is greater than the decrease in the radius of curvature of the first portion of the stylet.

19. The catheter of claim 14 wherein the distal tip comprises a tip component and the stylet is attached to the tip component.

20. The catheter of claim 14 wherein the working region includes a plurality of spaced-apart electrodes wherein a first electrode is spaced from the distal tip a distance greater than the distance between the first bend and the distal tip.

21. The catheter of claim 20 wherein the electrodes are spaced apart from each other approximately 4 mm.

22. The catheter of claim 21 wherein the first electrode is spaced approximately 1.5 cm from the distal tip.

23. A catheter for use in ablating tissue in the heart of a patient, the catheter having a sheath with a distal end region having a distal tip at the distal extremity of the distal end region, a deflection region proximal the distal tip and a working region proximal the deflection region, the catheter comprising:

a plurality of electrodes mounted to the working region;

a stylet having a distal end region having a preformed distal shape comprising a bend, the stylet being formed of a shape-retentive and resilient material such that the distal end region of the stylet changes shape upon the application of force and upon the removal of force, returns to the preformed shape, the stylet having a first portion with a first diameter in the distal end region proximal the bend and a second portion with a second diameter, less than the first diameter, in the distal end region distal the bend, the stylet housed within the sheath and attached to the distal end of the sheath such that the first portion is substantially coincident with the working region and the second portion is substantially coincident with the deflection region; and a tendon housed within the sheath and attached to the distal end of the sheath and positioned for axial displacement wherein movement of the tendon in the proximal direction decreases the radius of curvature of the first and second portions of the stylet.

* * * * *

UNITED STATES PATENT AND TRADEMARK OFFICE
CERTIFICATE OF CORRECTION

PATENT NO. : 6,146,381
DATED : Nov. 14, 2000
INVENTOR(S) : Wade A. Bowe, Robert C. Hayzelden, John A. Simpson It is certified that error appears in the above-identified patent and that said Letters Patent is hereby corrected as shown below:

Title page, in the title, change "DEFLECTING", to read --DISTRIBUTING--.

Page 1, in the title, change "DEFLECTING", to read --DISTRIBUTING--.

Signed and Sealed this

Twenty-ninth Day of May, 2001

Attest:

NICHOLAS P. GODICI

Attesting Officer     Acting Director of the United States Patent and Trademark Office